United States Patent
Nakane et al.

(10) Patent No.: US 12,039,722 B2
(45) Date of Patent: **\*Jul. 16, 2024**

(54) IMAGE ANALYSIS METHOD, STORAGE MEDIUM, IMAGE ANALYSIS DEVICE, AND IMAGE ANALYSIS SYSTEM

(71) Applicant: OSAKA UNIVERSITY, Osaka (JP)

(72) Inventors: Kazuaki Nakane, Osaka (JP);
Hirofumi Yamamoto, Osaka (JP);
Sachiko Nankumo, Osaka (JP);
Yasuyoshi Tsutsumi, Yamaguchi (JP)

(73) Assignee: OSAKA UNIVERSITY, Osaka (JP)

( * ) Notice: Subject to any disclaimer, the term of this patent is extended or adjusted under 35 U.S.C. 154(b) by 317 days.

This patent is subject to a terminal disclaimer.

(21) Appl. No.: 17/442,499

(22) PCT Filed: Feb. 12, 2020

(86) PCT No.: PCT/JP2020/005213
§ 371 (c)(1),
(2) Date: Sep. 23, 2021

(87) PCT Pub. No.: WO2020/195258
PCT Pub. Date: Oct. 1, 2020

(65) Prior Publication Data
US 2022/0156927 A1    May 19, 2022

(30) Foreign Application Priority Data

Mar. 26, 2019  (JP) .................................. 2019-059164

(51) Int. Cl.
*G06T 7/00* (2017.01)
*G16H 30/40* (2018.01)
*G16H 50/80* (2018.01)

(52) U.S. Cl.
CPC ............ *G06T 7/0012* (2013.01); *G16H 30/40* (2018.01); *G16H 50/80* (2018.01); *G06T 2207/30024* (2013.01); *G06T 2207/30096* (2013.01)

(58) Field of Classification Search
CPC ......... G06T 7/0012; G06T 2207/30024; G06T 2207/30096; G06T 2207/10056;
(Continued)

(56) References Cited

U.S. PATENT DOCUMENTS 5,257,182 A  * 10/1993 Luck .................... G06V 20/693
706/924
7,991,221 B1 *  8/2011 Kling ................ G06F 18/21375
382/154

(Continued)

FOREIGN PATENT DOCUMENTS

CN    107850586 A    3/2018
CN    108629761 A    10/2018
(Continued)

OTHER PUBLICATIONS

Chinese Office Action, and English Translation therefore, for Chinese Application No. 202080023436.6, dated Jul. 28, 2023, (17 pages).

(Continued)

*Primary Examiner* — Lewis G West
(74) *Attorney, Agent, or Firm* — Kagan Binder, PLLC

(57) ABSTRACT

By analyzing an image of a cell sample, whether a cell shown in the image is cancerous or not, the type of cancer, etc. are objectively and appropriately determined. An image analyzing device (1) includes: a binarizing section (41) which carries out a binarizing process a plurality of times with respect to a single captured image so as to generate a plurality of binarized images, the binarizing section carrying (Continued)

out the binarizing process each time the binarizing section varies a binarization reference value; a Betti number calculating section (42) which calculates a region number, which indicates the number of hole-shaped regions, with respect to each of the plurality of binarized images which have been generated; and a cancer determining section (43) which determines a type of cancer occurring in a cell included in tissue, on the basis of the binarization reference value which has been applied at a time of generation of one of the plurality of binarized images with respect to which one the region number has a given value.

7 Claims, 9 Drawing Sheets

(58) Field of Classification Search
CPC .......... G06T 7/11; G06T 7/136; G06T 7/194; G16H 30/40; G16H 50/80
See application file for complete search history.

(56) References Cited

U.S. PATENT DOCUMENTS

| | | | |
|---|---|---|---|
| 2005/0260583 A1 | 11/2005 | Jackway et al. | |
| 2008/0205764 A1* | 8/2008 | Iwai ..................... | G06V 10/421 382/190 |
| 2008/0267485 A1 | 10/2008 | Yokoyama et al. | |
| 2010/0034439 A1* | 2/2010 | Asano ..................... | G06T 7/12 382/128 |
| 2010/0209924 A1 | 8/2010 | Yamaguchi | |
| 2011/0274340 A1* | 11/2011 | Suzuki ................. | G06V 20/698 382/133 |
| 2013/0163870 A1 | 6/2013 | Cao et al. | |
| 2013/0230230 A1 | 9/2013 | Ajemba et al. | |
| 2018/0204324 A1* | 7/2018 | Kawaguchi ............ | G01N 33/48 |
| 2018/0315190 A1* | 11/2018 | Sasagawa ................ | G06N 3/08 |
| 2019/0012297 A1* | 1/2019 | Kobayashi ............... | G06F 17/16 |
| 2019/0180194 A1 | 6/2019 | Kobayashi et al. | |

FOREIGN PATENT DOCUMENTS

| | | | |
|---|---|---|---|
| JP | 2010193883 A | 9/2010 | |
| JP | 2011065253 A | 3/2011 | |
| WO | 2005121784 A1 | 12/2005 | |
| WO | 2010087112 A1 | 8/2010 | |

OTHER PUBLICATIONS

International Search Report and Written Opinion, and English Translation thereof, for International Application No. PCT/JP2020/005213, dated Apr. 21, 2020, (13 pages).
International Preliminary Report on Patentability for International Application No. PCT/JP2020/005213, dated Oct. 7, 2021, (7 pages).
Adcock et al., "Classification of hepatic lesions using the matching metric," Computer Vision and Image Understanding, vol. 121, pp. 36-42, 2014, (7 pages).
Nakane, "Cancer histological image analysis method via using topological index," Graduate School of Medicine, Osaka University, vol. 35, No. 1, pp. 48-54, ISSN:0287-3745, 2017, (20 pages).
E-Space English Abstract for JP 2010-193883 A.
E-Space English Abstract for WO 2005121784 A1.
E-Space English Abstract for WO 2010087112 A1.
Extended European Search Report for European Application No. 20776986.0, dated Nov. 28, 2022, (7 pages).
Chung et al., "Topological Fidelity and Image Thresholding: A Persistent Homology Approach", Journal of Mathematical Imaging and Vision, vol. 60, No. 7, pp. 1167-1179, Mar. 8, 2018, (13 pages).
Qaiser et al., "Persistent Homology for Fast Tumor Segmentation in Whole Slide Histology Images", Procedia Computer Science, vol. 90, pp. 119-124, Jul. 25, 2016, (6 pages).
Nakane et al., "Image Diagnosis for Large Intestinal Cancer by Use of Algorithm. Employing Combinatorial Logic Invariants", roceedings of JAMIT Annual Meeting 2010, pp. 16 (Year: 2010), (16 pages).
Nakane et. Al., "On the Classification of Colon Cancer Differentiation by Hierarchical Homology," The 14th General Meeting of the Japanese Society of Digital Pathology Program. Shorokushu, 28, GO-14, pp. 1-3, Sep. 10, 2015, (3 pages).
Nakane et al., "A simple mathematical model utilizing topological invariants for automatic detection of tumor areas in digital tissue images," Diagnostic Pathology, Article S27, Sep. 30, 2013, pp. 1-4, (4 pages).
Nakane et al., "Homology-based method for detecting regions of interest and colonic digital images," Diagnostic Pathology, 10:36, pp. 1-5, Apr. 24, 2015, (5 pages).
International Search Report and Written Opinion for International Application No. PCT/JP2016/070143, dated Sep. 6, 2016, (12 pages).
Chinese Second Office Action, and English Translation therefore, for Chinese Application No. 202080023436.6, mailed Mar. 27, 2024, (21 pages).

* cited by examiner

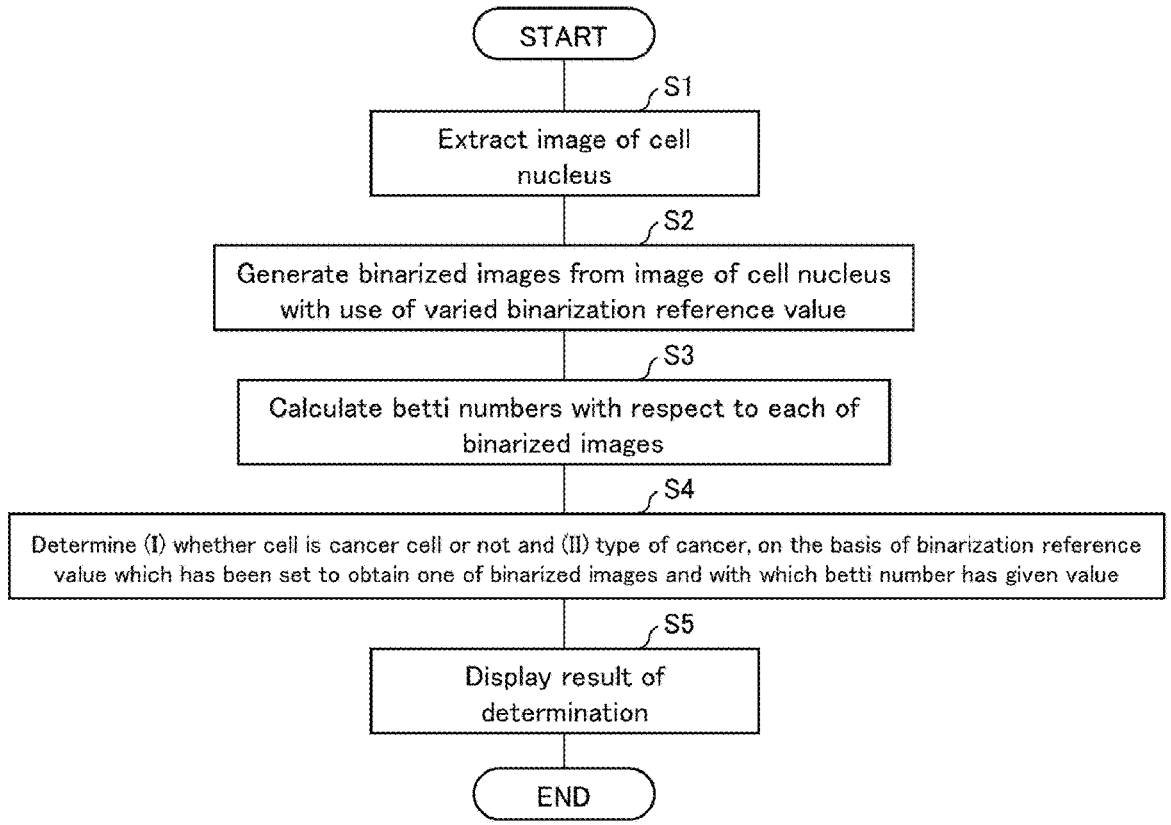
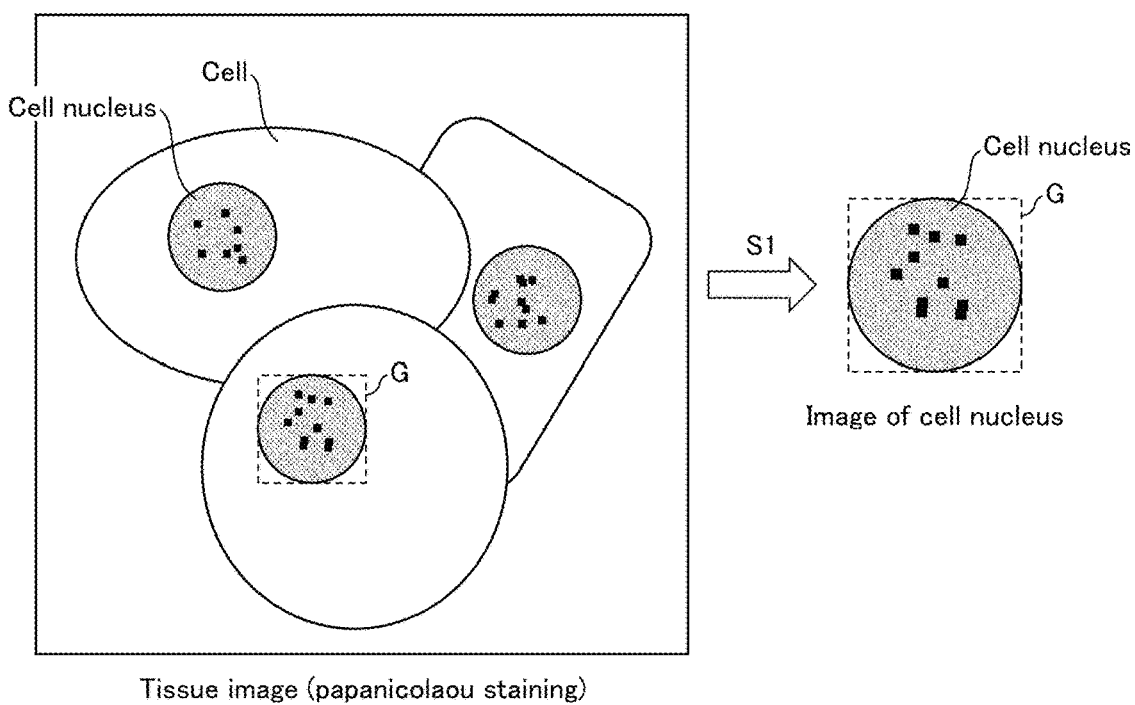

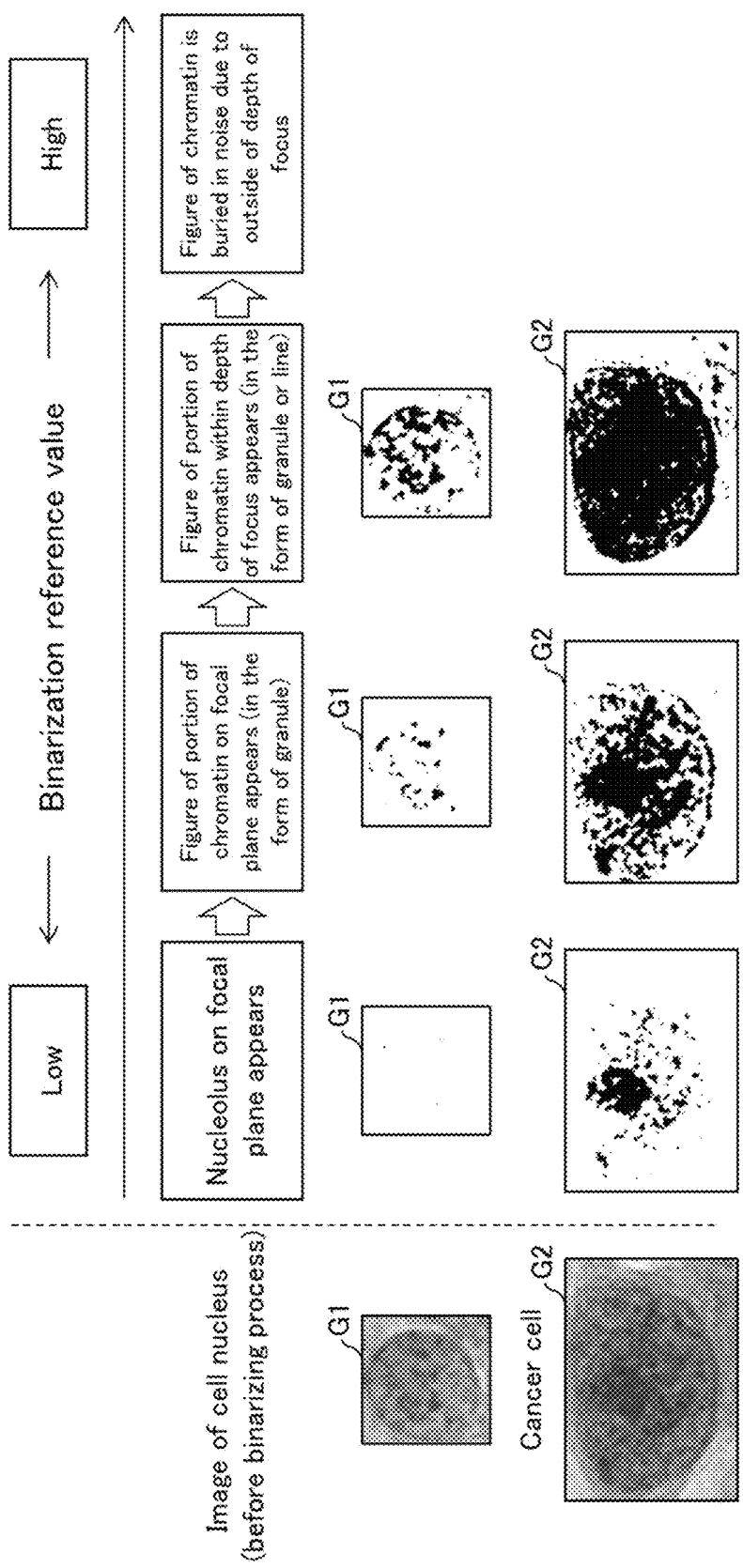

FIG. 11

| | | | | | | | | |
|---|---|---|---|---|---|---|---|---|
| S401 | | | YES 113 | | | | | NO 34 |
| | | | | | | | | To S403 |
| S404 | | | YES 74 | | | NO 38 | | |
| | | | | | | Yes 34 | No 4 | |
| | | | | | | 100% Normal cells | To S403 | |
| Result of determination of whether cells are cancer cells or not | | | 100% Cancer cells | | | | | |
| S405 | | | | | | | | |
| S407 | | | NO 55 | | YES 19 | | | |
| S409 | YES 33 | NO 22 | | | 94.7% Adenocarcinoma | | | |
| | | 90.9% Squamous cell carcinoma | | | | | | |
| S411 | NO 5 | YES 28 | | | | | | |
| | 6.7% Type of cancer cannot be determined | 82.1% Small cell carcinoma | | | | | | |

IMAGE ANALYSIS METHOD, STORAGE MEDIUM, IMAGE ANALYSIS DEVICE, AND IMAGE ANALYSIS SYSTEM

CROSS-REFERENCE TO RELATED APPLICATIONS

This application claims priority to International Application No. PCT/JP2020/005213, filed Feb. 12, 2020 and titled "IMAGE ANALYSIS METHOD, IMAGE ANALYSIS PROGRAM, RECORDING MEDIUM, IMAGE ANALYSIS DEVICE, AND IMAGE ANALYSIS SYSTEM," which in turn claims priority from a Japanese Patent Application having serial number 2019-059164 filed Mar. 26, 2019, titled "IMAGE ANALYSIS METHOD, IMAGE ANALYSIS PROGRAM, RECORDING MEDIUM, IMAGE ANALYSIS DEVICE, AND IMAGE ANALYSIS SYSTEM," both of which are incorporated herein by reference in their entireties.

TECHNICAL FIELD

The present invention relates to an image analyzing method, an image analyzing device, and an image analyzing system, each of which is for analyzing a captured image of tissue and identifying a cell which has cancerated.

BACKGROUND ART

It has been suggested to introduce a topological idea, in order to analyze, with use of computer technology, an image of, for example, a tissue slide which is used for a pathological diagnosis. As an example of a technique which assists a pathological diagnosis, Patent Literature 1 discloses an image analyzing device which extracts a cancer lesion with reference to a pathological image. The image analyzing device disclosed in Patent Literature 1 calculates, for each region, homology per unit area of the pathological image, and then determines whether or not each region is a target region (for example, a region which includes the cancer lesion).

Non-Patent Literature 1 discloses a method of analyzing, on the basis of a concept of persistent homology, a captured image of a liver and classifying a lesion in the liver.

CITATION LIST

Patent Literature

[Patent Literature 1]
WO2010/087112 (published on Aug. 5, 2010)

Non-Patent Literature

[Non-patent Literature 1]
Aaron Adcock et al., "Classification of Hepatic Lesions using the Matching Metric", Computer Vision and Image Understanding, Vol. 121, pp. 36-42, 2014.

SUMMARY OF INVENTION

Technical Problem

Generally, in an image diagnosis, early detection of a cancer cell is important. Therefore, in an image analyzing technique, a technique has been demanded which makes it possible to easily determine whether a cell which has been collected from a subject is a cancer cell or not.

In the case of, for example, lung cancer, there is a cancer cell which is classified as a small cell carcinoma. A small cell carcinoma rapidly progresses. Therefore, a cancer cell which is classified as a small cell carcinoma requires a prompt diagnosis and treatment. Thus, since some types of cancer cells require prompt diagnoses and treatment due to rapid progression of cancer, it is desirable to be able to determine the type of cancer in addition to the presence or absence of a cancer cell.

Generally, in a cancer cell, an increase in amount of chromatin is seen in a cell nucleus. Therefore, in a conventional cancer diagnosis, an increase in amount of chromatin in a cell nucleus is one of indicators of cancer. However, chromatin is distributed three-dimensionally in a cell nucleus. Therefore, it has been necessary to obtain a plurality of images of a cell which have been captured with a varied focal point, in order to three-dimensionally detect, as an image, an increase in amount of chromatin in the cell. However, it has been troublesome for, for example, a laboratory technician and a pathologist to obtain a plurality of images of a cell which have been captured with a varied focal point.

It is an object of an aspect of the present invention to more easily determine, by analyzing an image of a cell sample, whether a cell shown in the image is cancerous or not, the type of cancer, and the like.

Solution to Problem

In order to attain the above object, an image analyzing method in accordance with an aspect of the present invention is a method for analyzing a captured image of tissue, including: a binarizing step of carrying out a binarizing process a plurality of times with respect to a single captured image so as to generate a plurality of binarized images, the binarizing process being carried out in such a manner that each time a binarization reference value is varied, the binarizing process is carried out; a region number calculating step of calculating a region number, which indicates the number of hole-shaped regions, with respect to each of the plurality of binarized images which have been generated in the binarizing step; and a determining step of determining a type of cancer occurring in a cell included in the tissue, on the basis of the binarization reference value which has been applied at a time of generation of one of the plurality of binarized images with respect to which one the region number has a given value.

In order to attain the above object, an image analyzing device in accordance with an aspect of the present invention is an image analyzing device which analyzes a captured image of tissue, including: a binarizing section which carries out a binarizing process a plurality of times with respect to a single captured image so as to generate a plurality of binarized images, the binarizing section carrying out the binarizing process each time the binarizing section varies a binarization reference value; a region number calculating section which calculates a region number, which indicates the number of hole-shaped regions, with respect to each of the plurality of binarized images which have been generated; and a cancer determining section which determines a type of cancer occurring in a cell included in the tissue, on the basis of the binarization reference value which has been applied at a time of generation of one of the plurality of binarized images with respect to which one the region number has a given value.

Advantageous Effects of Invention

According to an aspect of the present invention, it is possible to more easily determine, by analyzing an image of a cell sample, whether a cell shown in the image is cancerous or not, the type of cancer, and the like.

BRIEF DESCRIPTION OF DRAWINGS

FIG. 3 is a flowchart illustrating an example of a flow of a process carried out by the image analyzing device.

FIG. 4 is a drawing schematically illustrating a process of extracting an image of a cell nucleus.

FIG. 5 is a drawing for explaining characteristics of binarized images which are generated by binarizing an image of a cell nucleus with use of a varied binarization reference value.

FIG. 11 is a drawing illustrating an example of a result of determination.

Figure 1:
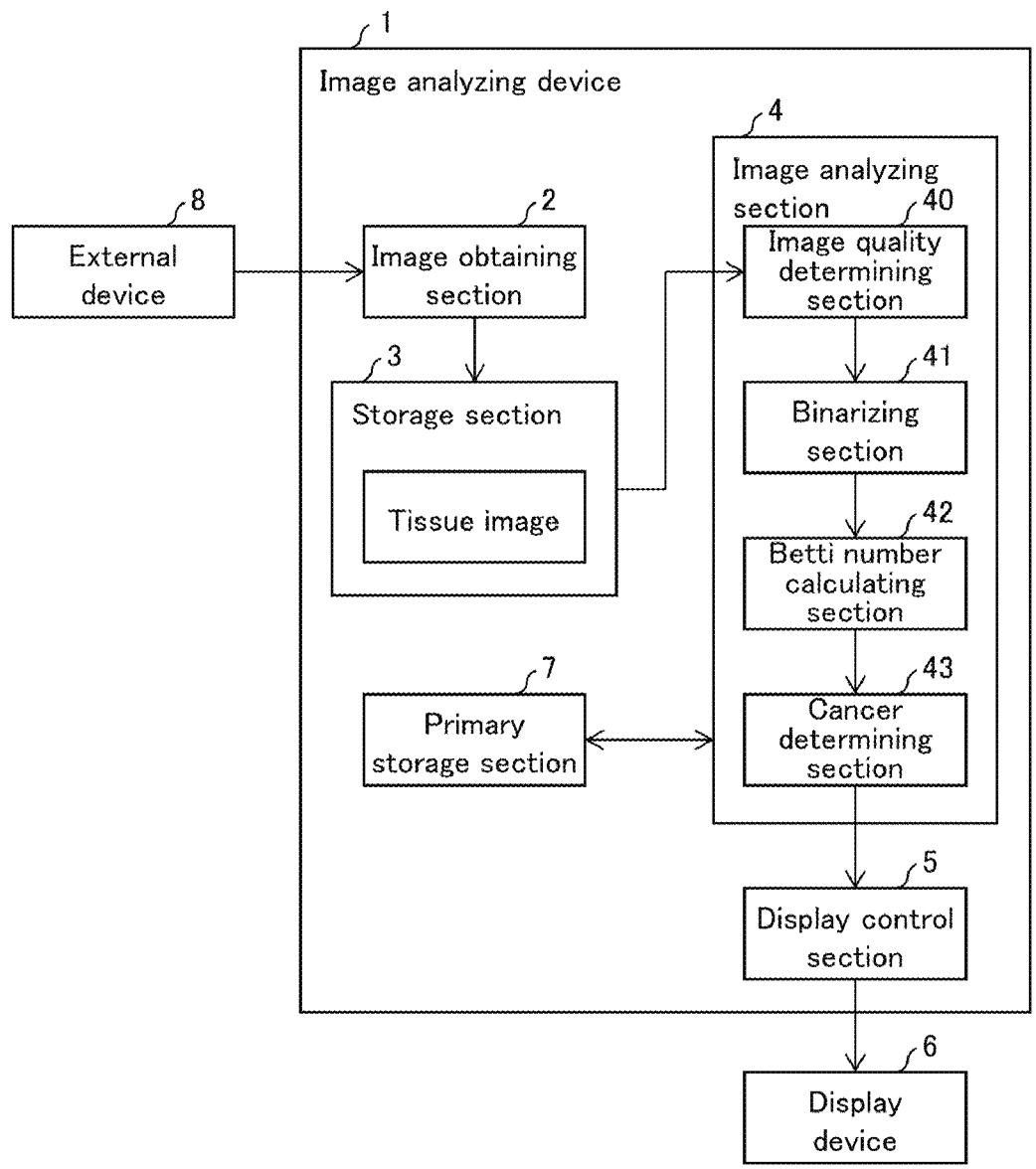
FIG. 1 is a block diagram illustrating a configuration example of an image analyzing device in accordance with Embodiment 1 of the present invention.

DESCRIPTION OF EMBODIMENTS (Technical Idea on Present Invention)

First, a technical idea on the present invention will be described below. The object of the present invention is to determine, by analyzing a captured image of tissue, the type of cancer occurring in the tissue shown in the captured image.

The inventors of the present invention examined a captured image of a preparation of a cell sample that had been stained by a given staining method, and made comparison and consideration in detail as to the following (1) through (3).

(1) Information pertaining to the amount of chromatin which amount was obtained from a captured image of a cell nucleus;
(2) Information pertaining to whether a cell was cancerous or not; and
(3) Information indicating correspondence between the captured image and the type of cancer.

Note, here, that the "cell sample" may be a sample which contains a cell that has been collected from tissue of a subject or may be alternatively a sample which contains a cell that has been isolated or detached from the tissue of the subject.

The inventors of the present invention carried out a binarizing process a plurality of times with respect to the captured image of the cell nucleus. In so doing, each time the inventors of the present invention varied a reference value for binarization (hereinafter, referred to as a binarization reference value), they carried out the binarizing process. The inventors of the present invention then examined a relationship between (i) the varied binarization reference value and (ii) a zero-dimensional Betti number b0 and a one-dimensional Betti number b1 which were indicated by figures of tissue that were included in images obtained by carrying out the binarizing process with use of the varied binarization reference value. As a result, the inventors of the present invention found it possible to determine (i) whether a cell is cancerous or not and (ii) the type of cancer, on the basis of a relationship between (a) a binarization reference value and (b) a zero-dimensional Betti number b0 and a one-dimensional Betti number b1 which are indicated by figures of tissue that are included in binarized images.

<Determination of Cancer by Cytologic Diagnosis>

Examples of characteristics found in a cancer cell include an increase in size of a cell nucleus and an increase in amount of chromatin. Note, here, that an increase in amount of chromatin indicates a state where the amount of chromatin is larger than the amount of chromatin in a normal cell during interphase (i.e., G1 phase—S phase—G2 phase). Chromatin is a substance which is present in cell nuclei of eukaryotes and which is well stained with a basic dye. Chromatin is a complex composed mainly of DNA and histones. It is also known that chromatin undergoes significant structural changes, such as condensation or decondensation, depending on a cell cycle and an activity status of a gene, etc.

In a cytologic diagnosis, the Papanicolaou staining method has been employed to make a preparation of a cell sample. However, a method of making a preparation of a cell sample is not limited to the Papanicolaou staining method. The Papanicolaou staining method is a method of staining a cell nucleus and cytoplasm. According to the Papanicolaou staining method, a cell smeared on a glass surface (e.g., a slide glass) is first wet-fixed with use of an alcohol before the cell becomes dry, and then a cell nucleus is stained with hematoxylin. Next, cytoplasm is stained with eosin, orange G, or light green. Chromatin is more deeply stained indigo by the hematoxylin than the other molecules in the cell nucleus. Therefore, a figure of the chromatin is observed in the form of a deeply-colored fine granule, coarse granule, or aggregate of a number of granules. Note that, similarly to the chromatin, a nucleolus is also deeply stained by the hematoxylin.

In a conventional cytologic diagnosis, an increase in amount of chromatin can be evaluated on the basis of the size of each granule (figure of chromatin), the number of granules (figure of chromatin), and a degree of aggregation of granules (figure of chromatin) in a captured image showing a cell nucleus. For example, it is determined that the amount of chromatin is increased in a case where, for example, (1) a granule has a large diameter, (2) a number of granules are present in a cell nucleus, and (3) a number of aggregates of granules are present.

However, since a captured image of a preparation of a cell sample is represented in a two-dimensional light-dark pattern, it is not possible to accurately grasp, from the captured image, a state of three-dimensional presence of chromatin in a cell nucleus.

<Figure of Chromatin in Captured Image>

Figure 14:
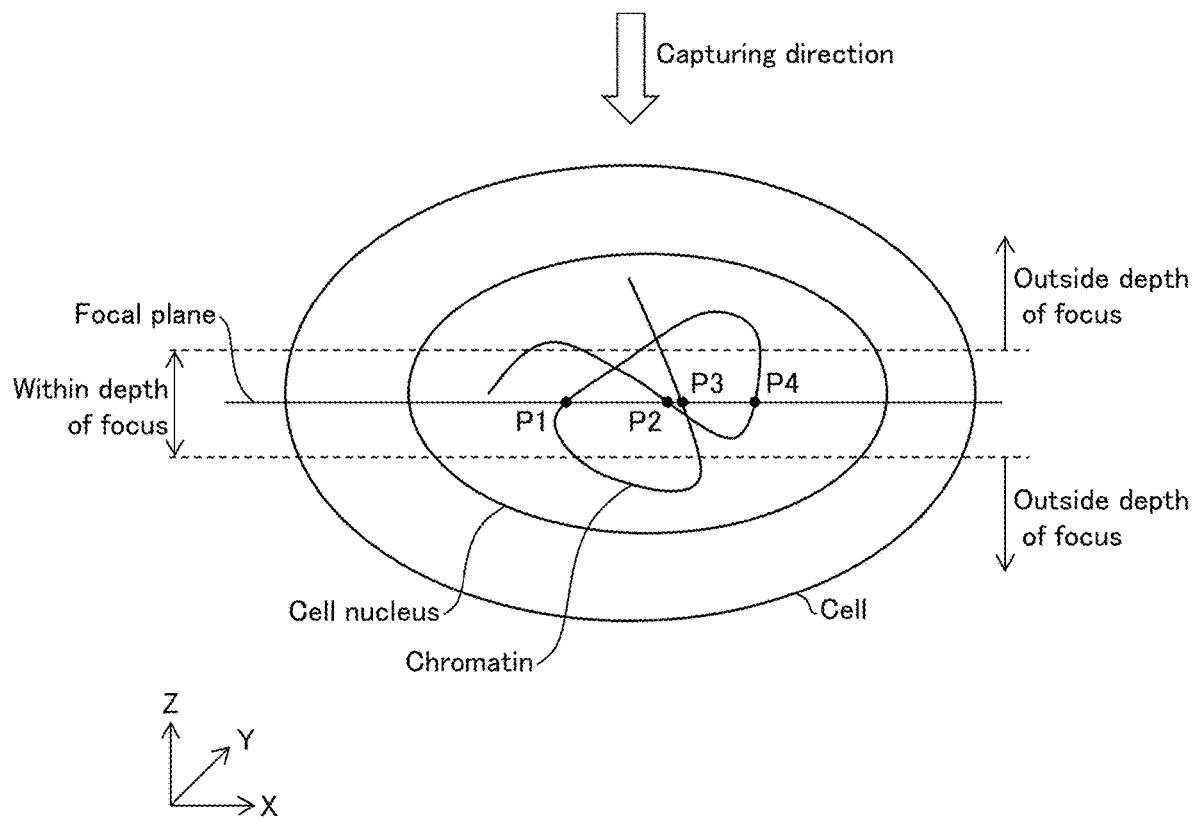
FIG. 14 is a conceptual diagram for explaining a relationship between a state of chromatin in a cell nucleus and a captured image of a cell.

A figure of chromatin in a captured image of a cell included in a cell sample will be described with reference to FIG. 14. FIG. 14 is a conceptual diagram for explaining a relationship between a state of chromatin in a cell nucleus and a captured image of a cell. Note that FIG. 14 is a cross-sectional view illustrating a cross section of the cell which cross section has been obtained by cutting the cell, the image of which is captured from a positive side of a z axis, along a plane including the z axis.

As illustrated in FIG. 14, the chromatin in the cell nucleus is considered to be linear and is distributed three-dimensionally in the cell nucleus. Portions of the chromatin which portions correspond to positions P1 through P4 on a focal plane are shown in the captured image as high-contrast and clear figures. Note that the "focal plane" indicates a plane which passes through a focal point of an optical system used for capturing and which is perpendicular to an optical axis of the optical system. Note also that figures of portions of the chromatin which portions are located on the near side and the far side of the focal plane within the depth of focus have lower contrast than the figures of the portions of the chromatin which portions correspond to the positions P1 through P4. A figure of a portion of the chromatin which portion is present further away from the focal plane (i.e., outside the depth of focus) is blurred and looks like a thin fog. This makes it difficult to distinguish the figure from figures of cytoplasm and the like. Note, here, that "high-contrast" indicates that brightness of a figure of chromatin greatly differs from the brightness of its surroundings in which the chromatin is not present. For example, a figure of stained chromatin becomes clearer and darker than a figure of its background, such as cytoplasm, as contrast becomes higher. On the other hand, as the contrast becomes lower, a difference between brightness of the figure of the stained chromatin and brightness of the figure of its background, such as the cytoplasm, becomes smaller.

The inventors focused their attention on the above relationship between the depth of focus and contrast. The inventors found that, by mathematically analyzing binarized images obtained by binarizing pixel values which relate to brightness of a captured image, it is possible to read information pertaining to a state of presence of chromatin which is three-dimensionally distributed in a cell nucleus. In a case where chromatin is linear and is three-dimensionally dispersed as illustrated in FIG. 14, the chromatin is considered to be present in a cell nucleus in a state of being interlaced and entangled like entangled yarn. In a case where the amount of the chromatin is increased, a degree of crowding and a degree of interlacing of the chromatin is increased. The degree of crowding and the degree of interlacing of the chromatin within the depth of focal can be evaluated by mathematically analyzing binarized images. Therefore, it is not necessary to obtain a plurality of images of a cell which have been captured with a varied focal point.

<Mathematical Representation for Evaluating Amount of Chromatin in Cell Nucleus>

In order to evaluate an increase in amount of chromatin in a cell nucleus on the basis of a degree of interlacing of the chromatin, the inventors of the present invention attempted to apply the concept of homology, in particular, persistent homology. Homology is one of mathematical fields which facilitates an analysis of, for example, connection between figures by substituting an algebraic expression for morphological characteristics of the figures. In particular, the inventors of the present invention focused their attention on use of a zero-dimensional Betti number and a one-dimensional Betti number among homology concepts.

The concept of homology is a mathematical concept indicative of contact between constituent elements. It is possible to evaluate a degree of crowding and a degree of interlacing of chromatin in a cell nucleus, by (i) setting a binarization reference value in relation to brightness of a captured image of a sample and (ii) calculating, from each binarized image, a zero-dimensional Betti number b0 and a one-dimensional Betti number b1 per cell nucleus.

A Betti number is a topological feature value which is independent of the shape of each of figures (constituent elements) but is dependent on merely contact and separation between the figures. In a case where a q-th singular homology group is finitely generated, the q-th singular homology group can be expressed by a direct sum of a free Abelian group and a finite Abelian group. A rank of the free Abelian group is called a "Betti number". In the case of figures in a two-dimensional plane, a zero-dimensional Betti number b0 indicates the number of connected components, and a one-dimensional Betti number b1 indicates the number of spaces ("hole-shaped regions") each of which is surrounded by a connected component(s), i.e., the number of "holes" present in the connected component(s).

<Zero-Dimensional Betti Number b0>

A zero-dimensional Betti number b0 is mathematically defined as follows. The number of connected components of a figure (also called a "one-dimensional complex") K obtained by connecting a finite number of line segments is generally referred to as a zero-dimensional Betti number b0. The expression "a figure obtained by connecting a finite number of points with use of a finite number of line segments is connected" means that it is possible to reach any second vertex from any first vertex of the figure by following a side of the figure.

A zero-dimensional Betti number b0 counted per cell nucleus in each binarized image reflects the number of granules which indicate distribution of chromatin in each cell nucleus. Therefore, it is considered that the zero-dimensional Betti number b0 counted per cell nucleus in each binarized image increases as the amount of the chromatin, which is three-dimensionally dispersed in each cell nucleus, increases.

<One-Dimensional Betti Number b1>

A one-dimensional Betti number b1 is mathematically defined as follows. A figure (one-dimensional complex) K obtained by connecting a finite number of line segments is assumed. Generally, in a case where opposite ends of a side "e" of K form different vertices, an operation of removing the side "e" and then making points at the opposite ends a single point is referred to as retraction. A figure obtained by carrying out this retraction with respect to a side(s) of the figure K with respect to which side(s) the retraction can be carried out is regarded as a figure K'. The number of sides of this K' is b1.

Figure 2:
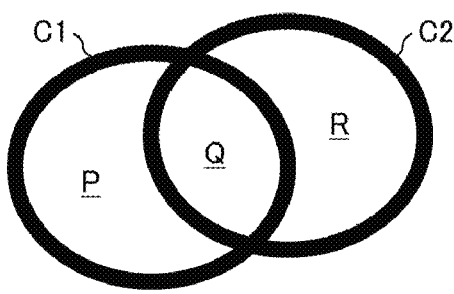
FIG. 2 is a drawing for explaining a one-dimensional Betti number which can be applied to the image analyzing device.

The one-dimensional Betti number will be described below with reference to a figure illustrated in FIG. 2. FIG. 2 is a drawing for explaining a Betti number which can be applied to an image analyzing device 1 in accordance with an embodiment of the present invention. According to FIG. 2, a circle C1 and a circle C2 intersect with each other. The number of "holes" in this figure is 3. A one-dimensional Betti number b1 calculated with respect to this figure is 3. Calculating a one-dimensional Betti number b1 with respect to a figure is thus equivalent to counting the number of "holes" in the figure.

A one-dimensional Betti number b1 counted per cell nucleus in each binarized image reflects the number of enclosed spaces which are formed in a case where a state of three-dimensional interlacing of chromatin in a cell nucleus is projected onto a plane. Therefore, it is considered that the one-dimensional Betti number b1 counted per cell nucleus in each binarized image increases as the amount of the chromatin, which is three-dimensionally dispersed in each cell nucleus, increases and a degree of interlacing of the chromatin increases.

Embodiment 1

Embodiment 1 of the present invention will be described in detail below. An example will be described below in which an image analyzing device 1 determines (i) whether a cell is lung cancer cell and (ii) the type of lung cancer. Note, however, that the present invention is applicable to determination of cancer occurring in tissue and a cell in each of which an increase in amount of chromatin is seen in a cell nucleus due to canceration, and an analysis object of the present invention is not limited to lung cancer. The image analyzing device 1 is applicable to determination of various types of cancer such as lung cancer, prostatic cancer, bladder cancer, breast cancer, thyroid cancer, ovarian cancer, cervical cancer, stomach cancer, pancreatic cancer, bile duct cancer, and malignant lymphoma.

Moreover, a cell sample may be any cell sample, provided that a nucleus in a cell can be observed. Furthermore, the cell sample does not depend on a collecting method. For example, in order to determine the type of lung cancer, it is possible to employ a captured image of an expectorated sputum sample, an endotracheally collected sputum sample, a transtracheally aspirated sputum sample, a sample obtained by bronchial scraping, a bronchial biopsy forceps lavage fluid, a mass impressed sample, a needle aspirated mass sample, or the like.

Note that a configuration in which a zero-dimensional Betti number b0 and a one-dimensional Betti number b1 are calculated will be described below. However, only any one of the zero-dimensional Betti number b0 and the one-dimensional Betti number b1 may be calculated and used. However, since chromatin is variously distributed in a cell nucleus and, accordingly, various characteristics appear in a captured image, it is preferable to calculate the zero-dimensional Betti number b0 and the one-dimensional Betti number b1. This is because, by detecting the amount of and a state of presence of chromatin in a cell nucleus on the basis of a change in the number of connected regions and a change in the number of hole-shaped regions in images of the cell nucleus, it is possible to accurately determine (i) whether a cell is a cancer cell or not and (ii) the type of cancer.

(Configuration of Image Analyzing Device 1)

A configuration of an image analyzing device 1 will be described below with reference to FIG. 1. FIG. 1 is a block diagram illustrating a configuration example of an image analyzing device 1 in accordance with Embodiment 1 of the present invention. As illustrated in FIG. 1, the image analyzing device 1 includes an image obtaining section 2, a storage section 3, an image analyzing section 4, a display control section 5, and a primary storage section 7. Note that, although FIG. 1 illustrates an example in which the image analyzing device 1 is connected to a display device 6 that is provided separately from the image analyzing device 1, the image analyzing device 1 is not limited to such a configuration. For example, the image analyzing device 1 may embed therein the display device 6. Alternatively, the image analyzing device 1 may be connected to a plurality of display devices 6 by wire or wireless.

The image obtaining section 2 obtains, from an external device 8, a captured image of tissue (hereinafter, referred to as a tissue image), and stores the obtained tissue image in the storage section 3. The external device 8 can be, for example, an image capturing device which is connected to a microscope or a server which stores therein or manages image data. The tissue image is obtained by capturing an image of the tissue at an appropriate magnification. Note that a magnification at which a tissue image is captured, i.e., a capturing magnification is preferably 1000 times. However, the capturing magnification at which a tissue image is captured can be set as appropriate by a person skilled in the art, depending on tissue which is to be analyzed, the number of pixels of the tissue image, and/or the like.

A method of staining tissue can be any method, provided that chromatin can be stained. For example, the above-described Papanicolaou staining method, an HE (Hematoxylin-Eosin) staining method, or the like can be employed. These staining methods are suitable for observation of chromatin in a cell nucleus in a cell, because the cell nucleus and cytoplasm are stained different colors and the chromatin is stained deeply.

The storage section 3 stores therein a tissue image which has been obtained by the image obtaining section 2. Furthermore, the storage section 3 stores therein (1) a control program for controlling each section, (2) an OS program, (3) an application program, and (4) various sets of data. The programs (1) through (3) are executed by the image analyzing section 4, and the various sets of data (4) are read out by the image analyzing section 4 in a case where the image analyzing section 4 executes these programs. The storage section 3 is constituted by a nonvolatile storage device such as a hard disk or a flash memory.

The primary storage section 7 is used as a working area in which data is temporarily stored while the programs are being executed. The temporary storage section 7 is constituted by a volatile storage device such as a random access memory (RAM).

The display control section 5 controls the display device 6 to display information which includes an analysis result that has been outputted by the image analyzing section 4.

The display device 6 displays information which includes an analysis result that has been outputted by the image analyzing section 4, and is, for example, a liquid crystal display. Note that the image analyzing device 1 can be configured so as to include a dedicated display device 6. Note also that the display device 6 can be configured such that a touch sensor is provided on a display screen of the display device 6 so that the display device 6 detects a touch operation conducted, by a user, with respect to a surface of the display screen.

(Configuration of Image Analyzing Section 4)

The image analyzing section 4 analyzes a tissue image which has been obtained by the image obtaining section 2, and determines (i) whether a cell included in the tissue image is cancerous or not and (ii) the type of cancer. The image analyzing section 4 include an image quality determining section 40, a binarizing section 41, a Betti number calculating section 42 (region number calculating section), and a cancer determining section 43.

The image quality determining section 40 determines whether a tissue image is suitable as an analysis object. Specifically, the image quality determining section 40 reads out a tissue image from the storage section 3, and analyzes frequency distribution of pixel values which relate to brightness of all pixels included in the tissue image. In a case where, in the frequency distribution of the pixel values which relate to the brightness, (i) a maximum does not occur at a plurality of pixel values and (ii) a pixel value at which a maximum occurs falls within a given range, the image quality determining section 40 determines that the tissue image is suitable as an analysis object. A tissue image which has been determined as being suitable by the image quality determining section 40 is analyzed by the image analyzing section 4.

FIG. 1 illustrates a configuration in which the image quality determining section 40 fetches a tissue image from the storage section 3. Note, however, that the present invention is not limited to such a configuration. For example, a tissue image which is to be analyzed and which has been obtained by the image obtaining section 2 may be outputted to the image quality determining section 40 without being stored in the storage section 3.

Next, the binarizing section 41 carries out a binarizing process with respect to an image of a cell nucleus which image has been standardized. Note, here, that the binarizing process is, for example, a process of (i) causing white color to be displayed by a pixel having a pixel value higher than a binarization reference value and (ii) causing black color to be displayed by a pixel having a pixel value equal to or lower than the binarization reference value. The binarizing section 41 generates a plurality of binarized images by carrying out the binarizing process, a plurality of times, with respect to a single image of a cell nucleus. In so doing, each time the binarizing section 41 varies the binarization reference value, the binarizing section 41 carries out the binarizing process.

Note that the binarizing section 41 may have a known image recognizing function (or image detecting function) and automatically extract an image of a cell nucleus on the basis of pixel values which indicate brightness of a tissue image. However, the present invention is not limited to such a configuration, and an image of a cell nucleus may be selected by, for example, a laboratory technician and/or a medical expert who use the image analyzing device 1. In this case, a tissue image may be displayed on a display screen of a display section of a computer which is used by the laboratory technician and/or the medical expert, and selection of an image of a cell nucleus by the laboratory technician and/or the medical expert may be accepted.

The Betti number calculating section 42 calculates, with respect to a plurality of binarized images which have been generated by the binarizing section 41, (1) the number of connected regions which are included in each of the plurality of binarized images and which are each formed by pixels that are connected to each other and that have a pixel value of 0 after binarization and (2) the number of hole-shaped regions (region number) which are included in each of the plurality of binarized images and which are each surrounded by pixels that have a pixel value of 0 after the binarization. That is, the Betti number calculating section 42 calculates a zero-dimensional Betti number b0 and a one-dimensional Betti number b1 with respect to a figure of a tissue which figure is included in each of the plurality of binarized images.

Each of the connected regions is, in each of the plurality of binarized images, a region in which a group of adjacent pixels display black color. Each of the connected regions is surrounded by pixels that display white color, and is visually recognized as a granular figure independent of another.

Each of the hole-shaped regions is, in each of the plurality of binarized images, a region in which pixels that display white color are surrounded by pixels that display black color. For example, in a case where pixels that display black color form a line, a hole-shaped region can be a hole surrounded by a black line.

An existing program can be employed as the Betti number calculating section 42. Examples of the exiting program encompass CHomP. The CHomP is freeware in compliance with the General Public License (GNU), and is available from a web site (http://chomp.rutgers.edu/). Note, however, that any program other than the CHomP can be employed, provided that the zero-dimensional Betti number and the one-dimensional Betti number can be calculated from an image.

Specifically, the Betti number calculating section 42 analyzes, with respect to each of images of cell nuclei, (i) correspondence between the zero-dimensional Betti number b0 and the binarization reference value and (ii) correspondence between the one-dimensional Betti number b1 and the binarization reference value. Then, the Betti number calculating section 42 calculates a binarization reference value Th1 with which the zero-dimensional Betti number b0 has a maximum value b0max, a binarization reference value Th2 with which the one-dimensional Betti number b1 comes to have a first given value, and a maximum value b1max of the one-dimensional Betti number b1. Note, here, that the binarization reference value Th2 is a binarization reference value at a time when the one-dimensional Betti number b1 first reaches the first given value in a case where the binarization reference value is gradually increased from 0. That is, the binarization reference value Th2 is the lowest one of values of the binarization reference value with which values the one-dimensional Betti number b1 has the first given value.

In a case where the binarization reference values Th1 and Th2 are calculated, it is desirable for the Betti number calculating section 42 to carry out a standardizing process with respect to pixel values. Note, here, that the standardizing process is a process for correcting the binarization reference values Th1 and Th2 depending on a degree of staining of each of cell samples and brightness of each of images of cell nuclei to be analyzed. Specifically, the Betti number calculating section 42 corrects the binarization reference values Th1 and Th2 so that, among pixel values which relate to brightness of each of images of cell nuclei, a pixel value which is the mode is 127. Note that 127 is a value intermediate between 0, which is a minimum pixel value, and 255, which is a maximum pixel value. By carrying out the standardizing process, it is possible for the Betti number calculating section 42 to appropriately calculate the binarization reference values Th1 and Th2 even in a case where there are variations of brightness among tissue images which variations are caused by differences in degree of staining among cell samples. Appropriately calculating the binarization reference values Th1 and Th2 is important to analyze each of images of cell nuclei and correctly evaluate the amount of chromatin in each of the cell nuclei.

For example, in a case where, in frequency distribution of pixel values which relate to brightness of an image of a certain cell nucleus, a pixel value which is the mode is Q, the Betti number calculating section 42 calculates the reference values Th1 and Th2 by the following equations.

(Reference value $Th1$ after correction)=(reference value $Th1$ before correction)−$\{Q-127\}$ (Reference value $Th2$ after correction)=(reference value $Th2$ before correction)−$\{Q-127\}$ In the following description, the binarization reference values Th1 and Th2 are corrected reference values Th1 and Th2, unless otherwise stated.

The cancer determining section 43 determines whether a cell included in tissue is a cancer cell or not, on the basis of (i) the binarization reference value Th2 with which the one-dimensional Betti number b1 comes to have the first given value and (ii) the maximum value b1max of the one-dimensional Betti number b1, each of which has been calculated by the Betti number calculating section.

The cancer determining section 43 may determine (i) whether a cell included in tissue is a cancer cell or not and (ii) the type of the cancer cell, on the basis of the following (1) through (4):
(1) the binarization reference value Th1 with which the zero-dimensional Betti number b0 has the maximum value b0max;
(2) the binarization reference value Th2 with which the one-dimensional Betti number b1 comes to have the first given value;
(3) the maximum value b1max of the one-dimensional Betti number b1; and
(4) one or more morphological characteristics of a cell nucleus.

Note that the one or more morphological characteristics of the cell nucleus can be, for example, the shape of the cell nucleus, the size of the cell nucleus, and/or the like. Note that an example will be described below in which the size of the cell nucleus is employed as the one or more morphological characteristics of the cell nucleus. In this case, the cancer determining section 43 may calculate the size of the cell nucleus by any method. For example, in a case where an image of the cell nucleus has the shape of a quadrangle, an actual size indicated by the length of a diagonal line or a side of the quadrangle may be calculated with use of a capturing magnification, and a value thus calculated may be used as a value indicating the size of the cell nucleus. Alternatively, the cancer determining section 43 may calculate, with use of the capturing magnification, the actual area of a region which is included in the image of the cell nucleus and which corresponds to the cell nucleus, and calculate the diameter of a circle having the same area as the area as the size of the cell nucleus.

(Flow of Process Carried Out by Image Analyzing Device 1)

Next, an example of a flow of a process carried out by the image analyzing device 1 will be described below with reference to FIG. 3. FIG. 3 is a flowchart illustrating an example of a flow of a process carried out by the image analyzing device 1. Note that a case where the binarizing section 41 has a function of extracting an image of a cell nucleus from a tissue image will be described here as an example.

First, the binarizing section 41 obtains a tissue image which has been determined as being suitable by the image quality determining section 40, and extracts an image G of a single cell nucleus from the obtained tissue image, as illustrated in FIG. 4 (step S1: extracting step). FIG. 4 is a drawing schematically illustrating a process of extracting an image of a cell nucleus. Note that the image G of the cell nucleus may be an image including only the single cell nucleus. Note also that the image G of the cell nucleus is preferably an image in which a region corresponding to the cell nucleus accounts for a given proportion (e.g., 85%) or more of the entire image of the cell nucleus. Although FIG. 4 illustrates an example in which a region which includes a single cell nucleus and which is enclosed by a rectangle G is extracted as the image G of the cell nucleus, a region which includes an entire cell nucleus and which is enclosed by any polygon, circle, or ellipse may be extracted as the image G of the cell nucleus.

The binarizing section 41 carries out a binarization process so as to generate a plurality of binarized images from the image of the cell nucleus which image has been extracted in the step S1 (step S2: binarizing step). In so doing, each time the binarizing section 41 varies a binarization reference value, the binarizing section 41 carries out the binarizing process.

FIG. 5 is a drawing for explaining characteristics of binarized images which are generated by binarizing an image of a cell nucleus with use of a varied binarization reference value. An image G1 of a cell nucleus is an image of a cell nucleus in a normal cell. On the other hand, an image G2 of a cell nucleus is an image of a cell nucleus in a cancer cell.

In a case where a binarization reference value is sufficiently low (e.g., 0), an image of a cell nucleus turns white in whole. In a case where the binarization reference value is gradually increased, figures of a nucleolus and the like which are present on a focal plane first appear in the form of granules or points. In a case where the binarization reference value is further increased, a figure of a portion of chromatin which portion is present on the focal plane appears. At this stage, a figure of the chromatin is in the form of a granule. In a case where the binarization reference value is further increased, a figure of a portion of the chromatin which portion is present within the depth of focus next appears. At this stage, the figure of the chromatin is in the form of a granule or a line. In a case where the binarization reference value is further increased, the figure of the chromatin in the cell nucleus is buried in noise due to the outside of the depth of focus. In a case where the binarization reference value is sufficiently high (e.g., 255), the image of the cell nucleus turns black in whole.

Such a tendency is seen in both (i) binarized images obtained from the image G1 of the cell nucleus in the normal cell and (ii) binarized images obtained from the image G2 of the cell nucleus in the cancer cell. However, as illustrated in FIG. 5, according to the binarized images obtained from the image G2 of the cell nucleus in the cancer cell, a granular figure and a linear figure of chromatin become obvious from when a binarization reference value is low, as compared with the binarized images obtained from the image G1 of the cell nucleus in the normal cell. Moreover, according to the binarized images obtained from the image G2 of the cell nucleus in the cancer cell, a figure of the chromatin is densely present, as compared with the binarized images obtained from the image G1 of the cell nucleus in the normal cell. This is because the amount of the chromatin in the cell nucleus in the cancer cell is increased, as compared with the amount of the chromatin in the cell nucleus in the normal cell.

Referring back to FIG. 3, the Betti number calculating section 42 then calculates a zero-dimensional Betti number b0 and a one-dimensional Betti number b1 with respect to each of the plurality of binarized images which have been generated by the binarizing section 41 (step S3: region number calculating step).

Figure 6:
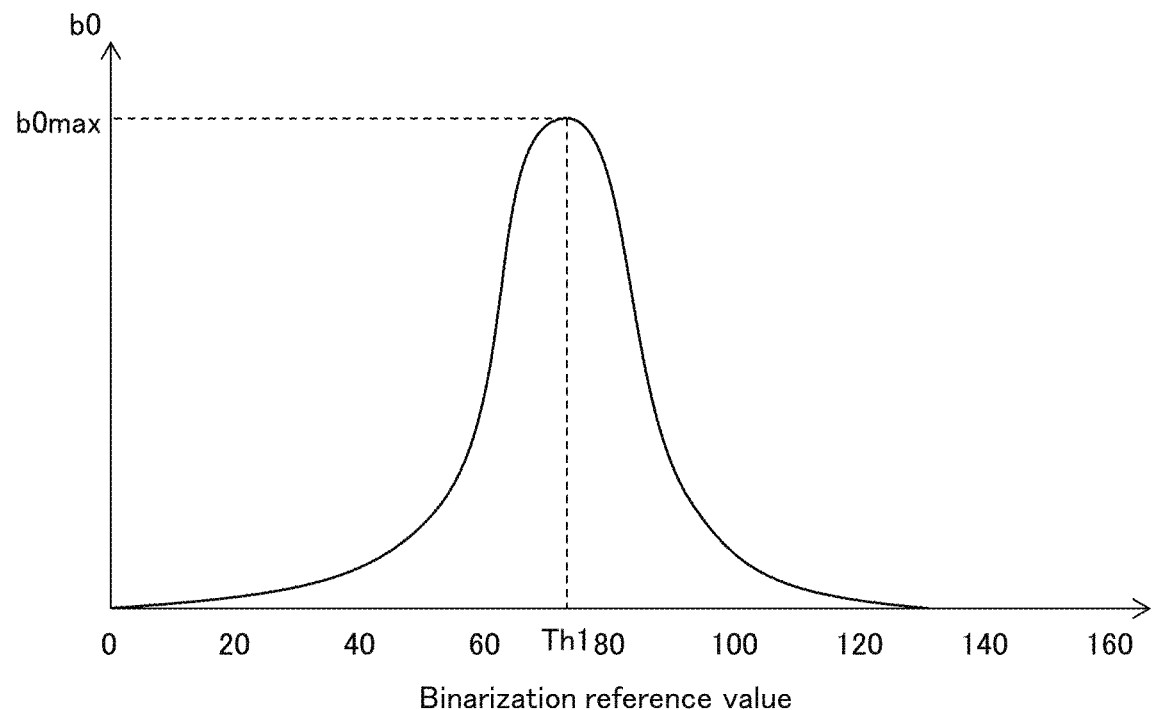
FIG. 6 is an example of a graph showing a relationship between (i) a zero-dimensional Betti number calculated with respect to each of images of a cell nucleus and (ii) a binarization reference value.

FIG. 6 is an example of a graph showing a relationship between (i) a zero-dimensional Betti number calculated with respect to each of images of a cell nucleus and (ii) a binarization reference value. As shown in FIG. 6, the zero-dimensional Betti number calculated with respect to each of the images of the cell nucleus gives a bell-shaped graph having a single maximum value b0max. For example, the Betti number calculating section 42 calculates a binarization reference value Th1 with which the zero-dimensional Betti number has the maximum value b0max (see FIG. 6).

Figure 7:
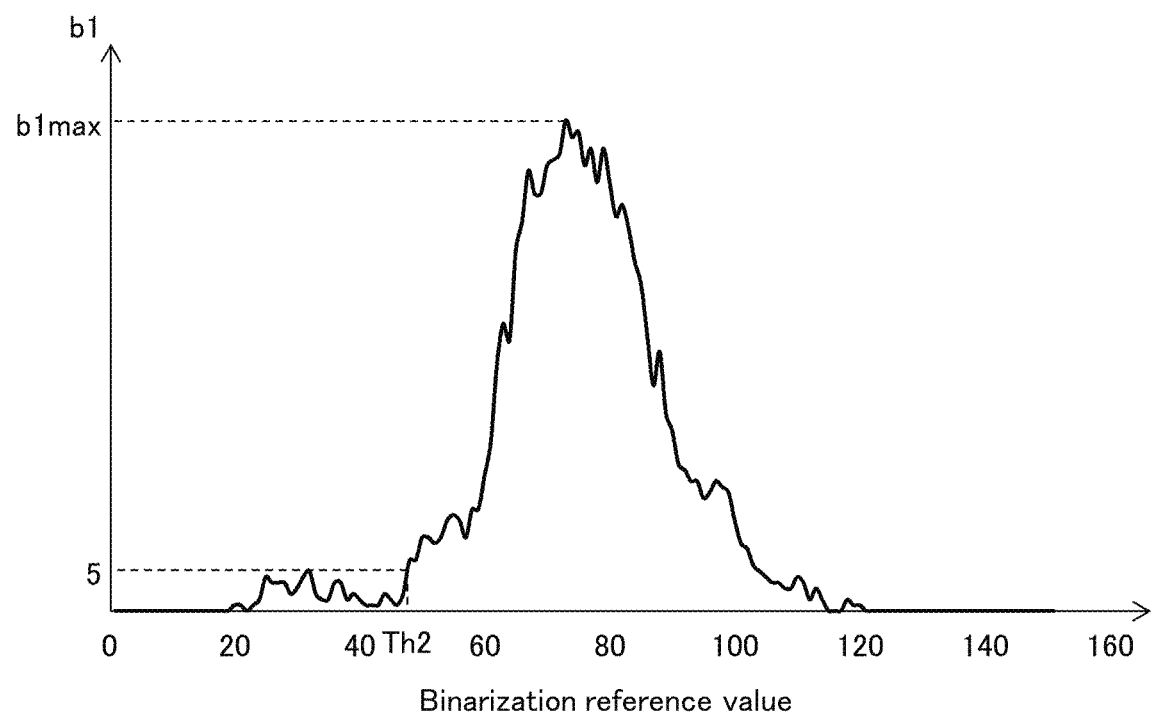
FIG. 7 is an example of a graph showing a relationship between (i) a one-dimensional Betti number calculated with respect to each of images of a cell nucleus and (ii) a binarization reference value.

FIG. 7 is an example of a graph showing the relationship between (i) a one-dimensional Betti number calculated with respect to each of images of a cell nucleus and (ii) a binarization reference value. As shown in FIG. 7, the one-dimensional Betti number calculated with respect to each of the images of the cell nucleus gives a bell-shaped graph having a single maximum value b1max. For example, the Betti number calculating section 42 calculates (i) a binarization reference value Th2 with which the one-dimensional Betti number b1 comes to have a first given value (e.g., b1=5) and (ii) the maximum value b1max of the one-dimensional Betti number b1 (see FIG. 7).

Referring back to FIG. 3, the cancer determining section 43 determines (i) whether a cell is cancerous or not and (ii) the type of cancer, on the basis of the binarization reference value which has been applied at a time of generation of one of the plurality of binarized images with respect to which one the one-dimensional Betti number b1, which has been calculated by the Betti number calculating section 42, has the first given value (step S4: determining step). A process carried out by the cancer determining section 43 will be described later with reference to specific examples.

The display control section 5 controls the display device 6 to display a result of determination which has been made by the cancer determining section 43 (step S6).

(Process of Determining Whether Cell is Cancer Cell or Not and Type of Cancer)

Figure 8:
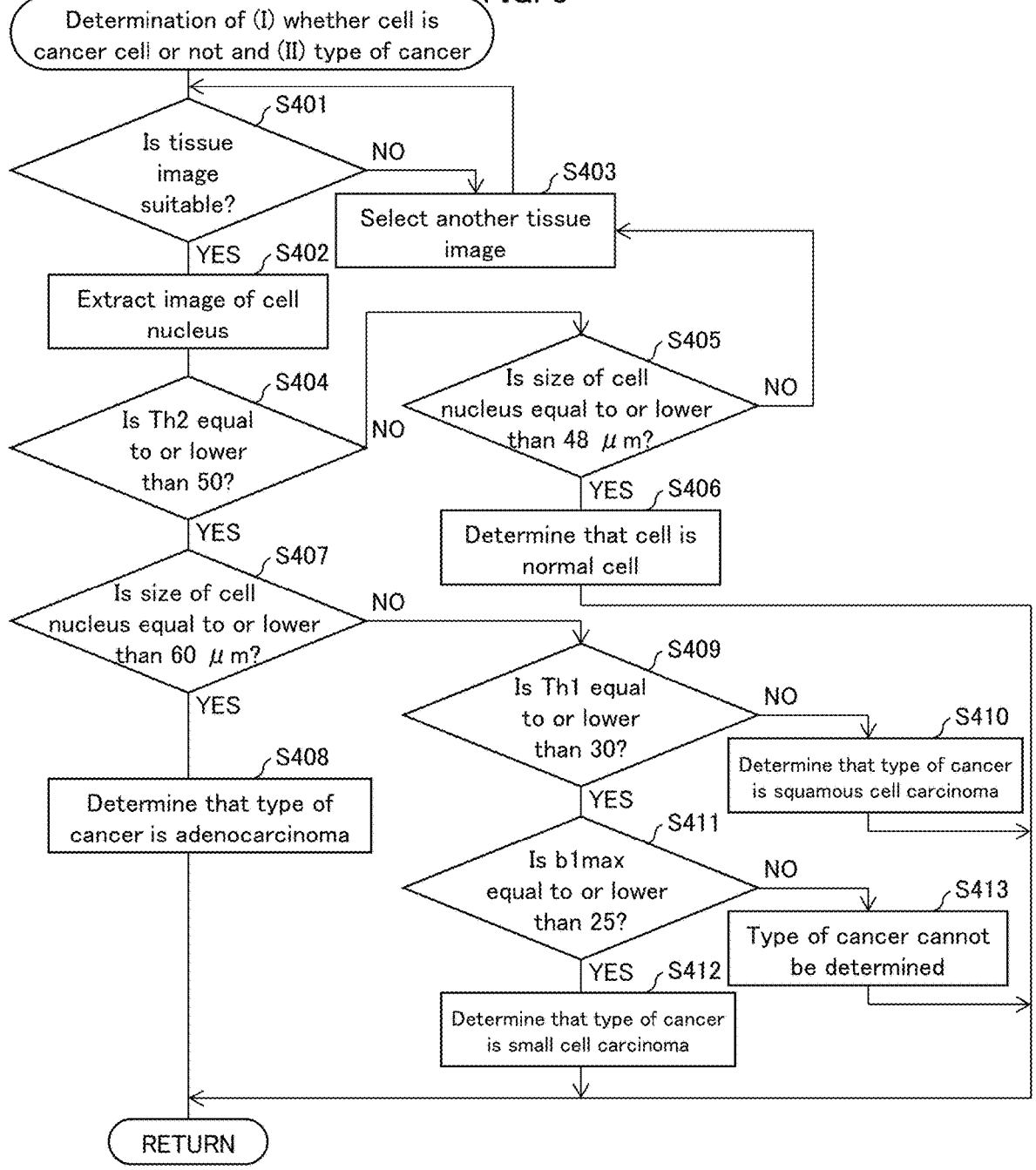
FIG. 8 is a flowchart illustrating an example of a flow of a cancer cell determining process.

Next, a specific example of a process of determining (i) whether a cell is a cancer cell or not and (ii) the type of cancer will be described with reference to FIG. 8. FIG. 8 is a flowchart illustrating an example of a flow of a cancer cell determining process. Note that determination order can be changed as appropriate, depending on a morphological characteristic of a cell to be subjected to the cancer cell determining process, the type of a cell to be subjected to determination, the type of cancer to be determined, and/or the like, and is not limited to the example illustrated in FIG. 8.

First, the image quality determining section 40 determines whether a tissue image is suitable as an analysis object (step S401). In a case where the image quality determining section 40 determines that the tissue image is not suitable as an analysis object (NO, in the step S401), the image quality determining section 40 selects another tissue image (step S403). Returning to the step S401, the image quality determining section 40 determines whether the another tissue image is suitable as an analysis object. Note that in a case where there is no other tissue images or in a case where determination of suitability as an analysis object has been made with respect to all tissue images, the image analyzing section 4 ends the process. Note also that although FIG. 8 illustrates, as an example, a case where, immediately before an image of a cell nucleus is extracted, the image quality determining section 40 determines whether a tissue image is suitable for an analysis, the present invention is not limited to such a configuration. For example, the image quality determining section 40 may determine whether a tissue image is suitable for an analysis, at any timing before an image of a cell nucleus is extracted.

In a case where the image quality determining section 40 determines that the tissue image is suitable as an analysis object (YES, in the step S401), the binarizing section 41 extracts an image of a cell nucleus (step S402). The Betti number calculating section 42 analyzes the extracted image of the cell nucleus, and calculates (i) a binarization reference value Th1 with which a zero-dimensional Betti number has a maximum value b0max, (ii) a binarization reference value Th2 with which a one-dimensional Betti number b1 comes to have a first given value (e.g., b1=5), and (iii) a maximum value b1max of the one-dimensional Betti number b1 (see step S3 in FIG. 3). The cancer determining section 43 also calculates the size of the cell nucleus on the basis of the extracted image of the cell nucleus and a capturing magnification. The binarization reference values Th1 and Th2, the maximum value b1max of the one-dimensional Betti number b1, and the size of the cell nucleus thus calculated are used in the following determination which is made by the cancer determining section 43.

Next, the cancer determining section 43 determines whether the binarization reference value Th2 is equal to or lower than a first threshold (step S404). In a case where whether a cell is a lung cancer cell is determined, the first threshold may be, for example, 50. In a case where the binarization reference value Th2 is higher than the first threshold (NO, in step S404), the cancer determining section 43 next determines whether the size of the cell nucleus is equal to or lower than a second threshold (step S405). In a case where the cancer determining section 43 determines that the size of the cell nucleus is equal to or lower than the second threshold (YES, in step S405), the cancer determining section 43 determines that a cell having the cell nucleus is a normal cell (or is not a cancer cell) (step S406). In a case where the cancer determining section 43 determines that the size of the cell nucleus is higher than the second threshold (NO, in step S405), the process returns to the step S403. The second threshold may be any threshold that makes it possible to distinguish between a normal cell and a cancer cell. For example, in the case of a lung, the second threshold may be 48 μm.

<First Threshold>

Figure 9:
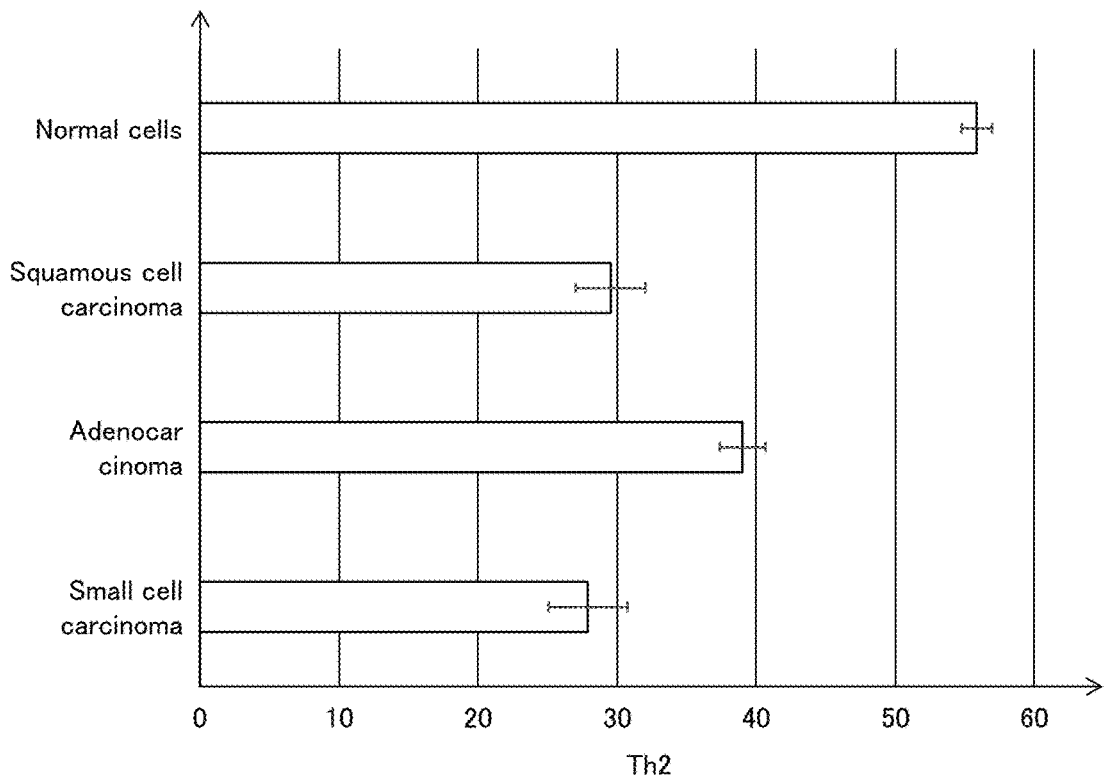
FIG. 9 is a drawing illustrating an example in which binarization reference values Th2 calculated with respect to normal cells and various types of cancer cells are compared.

The first threshold will be described below with reference to FIG. 9. FIG. 9 is a drawing illustrating an example in which binarization reference values Th2 calculated with respect to normal cells and various types of lung cancer cells are compared. For comparison, 40 normal cells, 29 cells classified as a squamous cell carcinoma, 35 cells classified as an adenocarcinoma, and 37 cells classified as a small cell carcinoma were used.

The binarization reference value Th2 with respect to the normal cells was 55.9±1.10. The binarization reference value Th2 with respect to the cells classified as a squamous cell carcinoma was 29.5±2.51. The binarization reference value Th2 with respect to the cells classified as an adenocarcinoma was 39.0±1.64. The binarization reference value Th2 with respect to the cells classified as a small cell carcinoma was 27.9±2.85. These binarization reference values Th2 are each expressed as a mean value±a standard error.

For example, it is assumed that Th=50 is employed as the first threshold. In a case where the binarization reference value Th2 is higher than 50, the cancer determining section 43 can determine that the cell is highly likely to be a normal cell. In a case where the binarization reference value Th2 is not higher than 50, the cancer determining section 43 can determine that the cell is highly likely to be a cancer cell.

Referring back to FIG. 8, in a case where the binarization reference value Th2 is equal to or lower than the first threshold (YES in the step S404), the cancer determining section 43 next determines whether the size of the cell nucleus is equal to or lower than a third threshold (step S407). In a case where the size of the cell nucleus is equal to or lower than the third threshold (YES, in the step S407), the cancer determining section 43 determines that the type of cancer occurring in the cell having the cell nucleus is an adenocarcinoma (step S408). The third threshold may be any threshold that makes it possible to distinguish between a cancer cell classified as an adenocarcinoma and a cancer cell classified as the other types of cancer. For example, the third threshold may be set to 60 μm.

In a case where the size of the cell nucleus is higher than the third threshold (NO, in the step S407), the cancer determining section 43 then determines whether the binarization reference value Th1 is equal to or lower than a fourth threshold (step S409). In a case where the binarization reference value Th1 is higher than the fourth threshold (NO, in step S409), the cancer determining section 43 determines that the type of the cancer occurring in the cells having the cell nucleus is a squamous cell carcinoma (step S410). The fourth threshold may be any threshold that makes it possible to distinguish between a cancer cell classified as a squamous cell carcinoma and a cancer cell classified as a small cell carcinoma. For example, the fourth threshold may be set to 30. For example, in a case where the binarization reference value Th1 =30 is employed as the fourth threshold, the cancer determining section 43 determines as follows in the step 409.

In a case where the binarization reference value Th1 is higher than 30, it is highly likely that the cancer is a squamous cell carcinoma.

In a case where the binarization reference value Th1 is equal to or lower than 30, the cancer is highly likely to be a small cell carcinoma.

In a case where the binarization reference value Th1 is equal to or lower than the fourth threshold (YES, in the step S409), the cancer determining section 43 then determines whether the maximum value b1max of the one-dimensional Betti number is equal to or lower than a fifth threshold (step S411). In a case where the maximum value b1max of the one-dimensional Betti number is equal to or lower than the fifth threshold (YES, in the step S411), the cancer determining section 43 determines that the type of the cancer occurring in the cell having cell nucleus is a small cell carcinoma (step S412). The fifth threshold may be any threshold that makes it possible to distinguish between a cancer cell classified as a small cell carcinoma and a cancer cell which is not classified as a small cell carcinoma. For example, the fifth threshold may be set to 25.

<Fifth Threshold>

Figure 10:
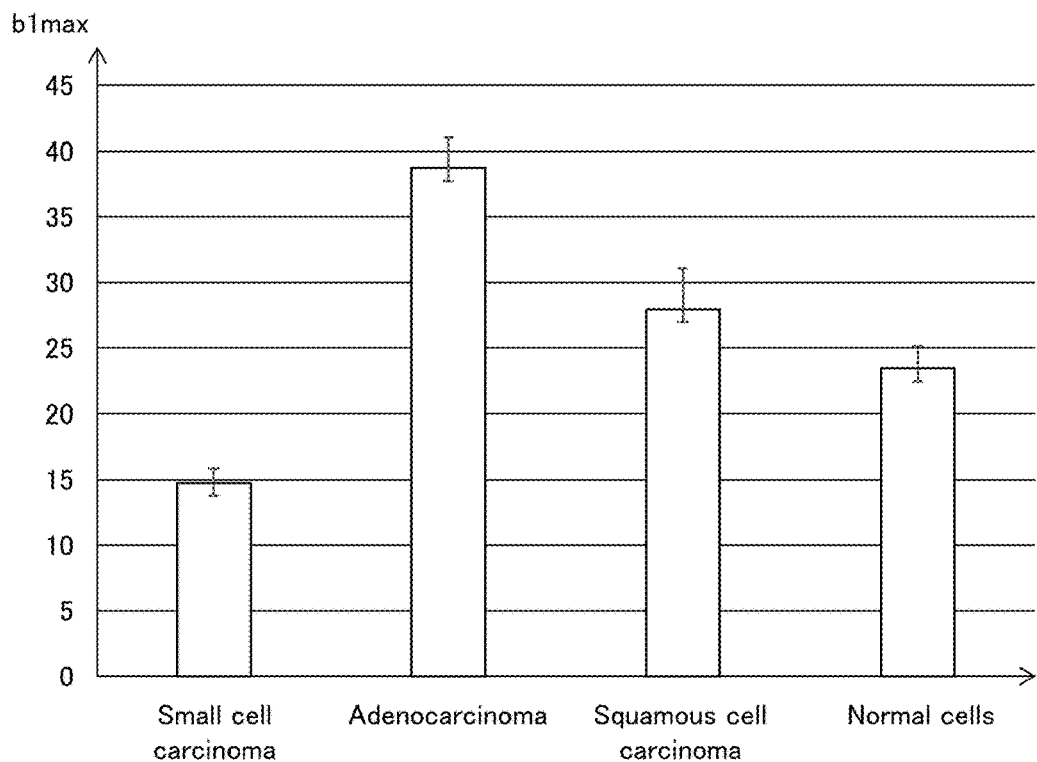
FIG. 10 is a drawing illustrating an example in which maximum values b1max of one-dimensional Betti numbers calculated with respect to normal cells and various types of cancer cells are compared.

The fifth threshold will be described below with reference to FIG. 10. FIG. 10 is a drawing illustrating an example in which maximum values b1max of one-dimensional Betti numbers calculated with respect to normal cells and various types of cancer cells are compared. For comparison, 40 normal cells, 29 cells classified as a squamous cell carcinoma, 35 cells classified as an adenocarcinoma, and 37 cells classified as a small cell carcinoma were used.

The maximum values b1max of the one-dimensional Betti numbers with respect to these cells were as follows.
Normal cells: 23.5±1.68
Cells classified as squamous cell carcinoma: 28.0±3.11
Cells classified as adenocarcinoma: 38.7±2.27
Cells classified as small cell carcinoma: 14.8±1.08
These maximum values b1max of the one-dimensional Betti numbers are each expressed as a mean value±a standard error.

For example, it is assumed that b1max=25 is employed as the fifth threshold. In a case where the maximum value b1max of the one-dimensional Betti number is not higher than 25, it can be determined that the cell is highly likely to be a normal cell or a cell classified as a small cell carcinoma. In a case where the maximum value b1max of the one-dimensional Betti number is higher than 25, it can be determined that the cell is less likely to be a cell classified as a small cell carcinoma. Since the cell determined as YES in the step S404 in FIG. 8 does not include a normal cell, the cell determined as YES in the step S411 is highly likely to be a cell classified as a small cell carcinoma.

Referring back to FIG. 8, in a case where the maximum value b1max of the one-dimensional Betti number is higher than the fifth threshold (NO, in the step S411), the cancer determining section 43 outputs a result of determination that the type of the cancer occurring in the cell having the cell nucleus cannot be determined (step S413).

In a case where it is possible to extract a plurality of images of cell nuclei from a single tissue image, the process carried out in the steps S404 through S413 may be carried out with respect to each of the plurality of images of the cell nuclei. This makes it possible to more accurately determine the type of cancer on the basis of a result of determination of the type of cancer made with respect to each of cells shown in the tissue image.

EXAMPLES

FIG. 11 is a drawing illustrating an example of a result of determination made in a case where a process of determining (i) whether cells were cancer cells or not and (ii) the type of cancer was carried out in accordance with the flowchart illustrated in FIG. 8. Note that 147 tissue images were used and that determination of (i) whether cells shown in each of the tissue images were normal cells or not and (ii) as what type of cancer cancer cells were classified had been made in advance by a pathologist et al. An image of a single cell nucleus was extracted from each of the tissue images.

Among the 147 tissue images used, 113 tissue images were determined as being suitable as analysis objects by the image quality determining section 40 (see the step S401 in FIG. 8). An image of a cell nucleus was extracted from each of the 113 tissue images, and used in a subsequent process. The other 34 tissue images were not analyzed (see the step S403 in FIG. 8).

Among 113 images of cell nuclei which images had been analyzed, 74 images of the cell nuclei were determined as YES by the cancer determining section 43 in the step S404 in FIG. 8, and 38 images of the cell nuclei were determined as NO. All of the 74 images of the cell nuclei which images were determined as YES by the cancer determining section 43 in the step S404 in FIG. 8 were images derived from the tissue images with respect to each of which the pathologist had determined in advance that cells shown in the each of the tissue images were cancer cells (accuracy of determination: 100%). On the other hand, among the 38 images of the cell nuclei which images were determined as NO by the cancer determining section 43 in the step S404 in FIG. 8, all of 34 images of the cell nuclei were images derived from the tissue images with respect to each of which the pathologist had determined in advance that cells shown in the each of the tissue images were normal cells (accuracy of determination: 100%). Note that the other 4 images of the cell nuclei were determined as NO in the step 405 and were not analyzed (see the step S403 in FIG. 8).

Among the 74 images of the cell nuclei, 55 images of the cell nuclei were determined as NO by the cancer determining section 43 in the step S407 in FIG. 8, and 19 images of the cell nuclei were determined as YES. Among the 19 images of the cell nuclei which images were determined as YES by the cancer determining section 43 in the step S407 in FIG. 8, 18 images of the cell nuclei were images derived from the tissue images with respect to each of which the pathologist had determined in advance that cells shown in the each of the tissue images were cancer cells classified as an adenocarcinoma (accuracy of determination: 94.7%).

Among the 55 images of the cell nuclei, 33 images of the cell nuclei were determined as YES by the cancer determining section 43 in the step S409 in FIG. 8, and 22 images of the cell nuclei were determined as NO. Among the 22 images of the cell nuclei which images were determined as NO by the cancer determining section 43 in the step S409 in FIG. 8, 20 images of the cell nuclei were images derived from the tissue images with respect to each of which the pathologist had determined in advance that cells shown in the each of the tissue images were cancer cells classified as a squamous cell carcinoma (accuracy of determination: 90.9%).

Among the 33 images of the cell nuclei, 28 images of the cell nuclei were determined as YES by the cancer determining section 43 in the step S411 in FIG. 8, and 5 images of the cell nuclei were determined as NO. Among the 28 images of the cell nuclei which images were determined as YES by the cancer determining section 43 in the step S411 in FIG. 8, 23 images of the cell nuclei were images derived from the tissue images with respect to each of which the pathologist had determined in advance that cells shown in the each of the tissue images were cancer cells classified as a small cell carcinoma (accuracy of determination: 82.1%). Note that, in regard to the other 5 images of the cell nuclei which images were determined as NO, the cancer determining section 43 determined that it was not possible to determine the type of cancer (see the step S413 in FIG. 8). A breakdown of the other 5 images of the cell nuclei was as follow: 1 image was an image derived from the tissue image with respect to which the pathologist had determined in advance that cells shown in the tissue image were cancer cells classified as a small cell carcinoma; 1 image was an image derived from the tissue image with respect to which the pathologist had determined in advance that cells shown in the tissue image were cancer cells classified as an adenocarcinoma; and 3 images were images derived from the tissue images with respect to each of which the pathologist had determined in advance that cells shown in the each of the tissue images were cancer cells classified as a squamous cell carcinoma.

Thus, it was revealed that the image analyzing device 1 was capable of highly accurately determining (i) whether a cell was a cancer cell or not and (ii) the type of the cancer cell.

Embodiment 2

Embodiment 2 of the present invention will be described below. Note that for convenience, members which have functions identical to those of the members described in Embodiment 1 are given respective identical reference numerals, and the members will not be described.

(Configuration of Image Analyzing Device 1a)

Figure 12:
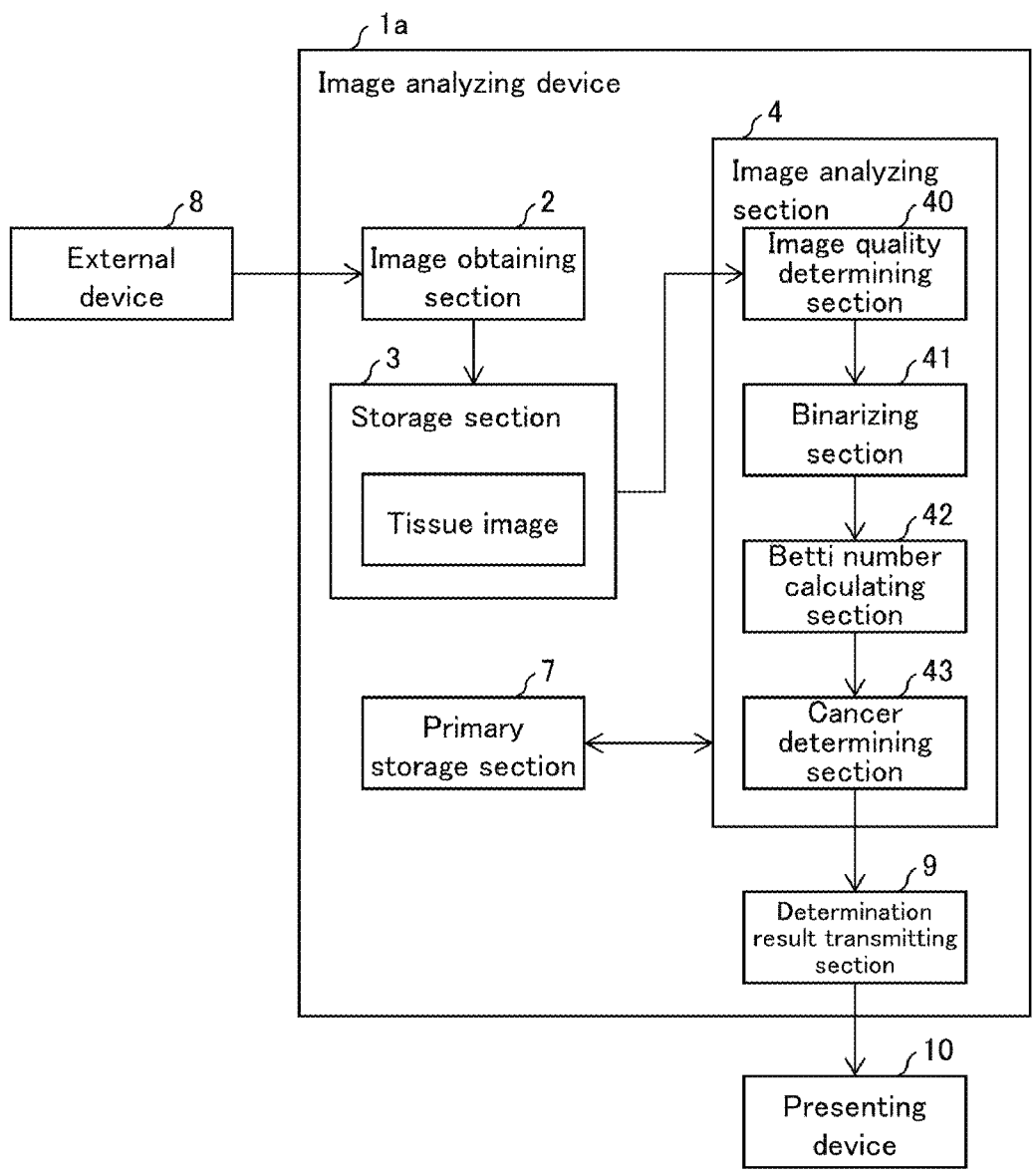
FIG. 12 is a block diagram illustrating a configuration example of an image analyzing device in accordance with Embodiment 2 of the present invention.

Next, a configuration of an image analyzing device 1a will be described below with reference to FIG. 12. FIG. 12 is a block diagram illustrating a configuration example of an image analyzing device 1a in accordance with Embodiment 2 of the present invention. The image analyzing device 1a is different from the image analyzing device 1 in that the image analyzing device 1a includes a determination result transmitting section 9, instead of a display control section 5. The determination result transmitting section 9 obtains, from a cancer determining section 43, a result of an analysis of a captured image which is indicated by image data received from an external device 8, and transmits the result to a presenting device 10. Note that the image analyzing device 1a can include a plurality of external devices 8 and a plurality of presenting devices 10.

(Image Analyzing System)

Figure 13:
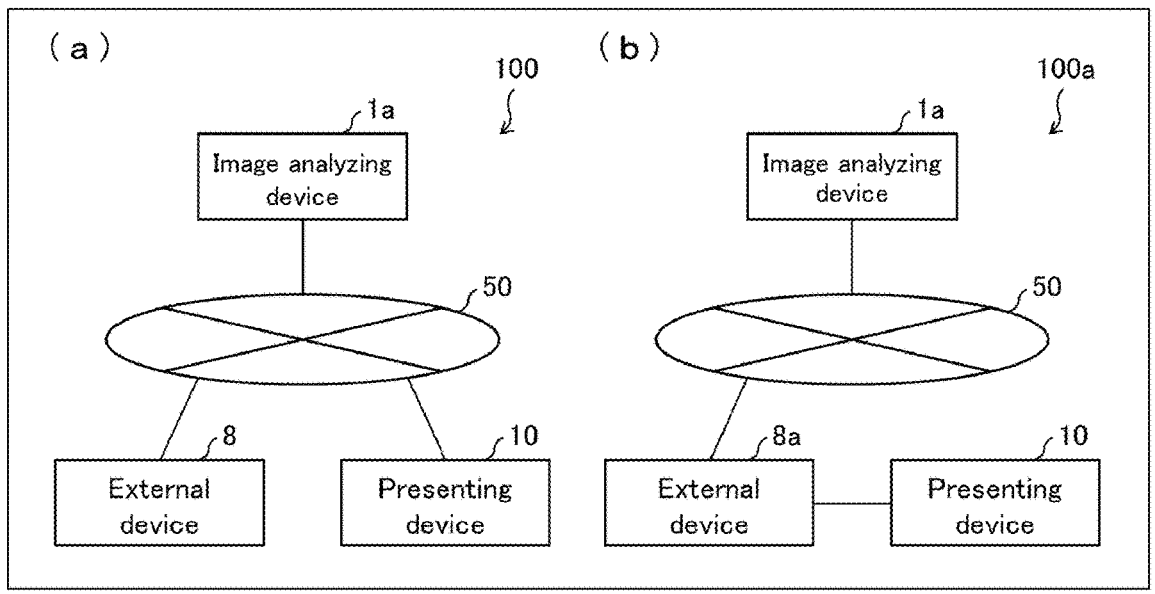
FIG. 13 is a drawing schematically illustrating configuration examples of image analyzing systems each of which includes an image analyzing device in accordance with an embodiment of the present invention.

Configuration examples of image analyzing systems 100 and 100a each of which includes an image analyzing device 1a will be described with reference to FIG. 13. FIG. 13 is a drawing schematically illustrating configuration examples of image analyzing systems 100 and 100a each of which includes an image analyzing device 1a in accordance with an embodiment of the present invention. (a) of FIG. 13 illustrates an example in which an external device 8 is provided in a place distant from a place in which a presenting device 10 is provided. (b) of FIG. 13 illustrates an example in which a presenting device 10 is connected to an external device 8a.

The image analyzing system 100 includes the external device 8, the image analyzing device 1a, and the presenting device 10. The external device 8, the image analyzing device 1a, and the presenting device 10 are each connected to an information communication network 50 such as the Internet. This allows the external device 8, the image analyzing device 1a, and the presenting device 10 to transmit/receive data to/from each other.

The external device 8 may be a device which has a function of capturing an image of tissue (e.g., microscope) or may be alternatively a server which integrally manages captured images of tissue (e.g., electronic medical record server, microscope image data server).

The presenting device 10 is not limited to any particular one, provided that the presenting device 10 is a device which has a function of presenting, to a user, a result of an analysis of an image. The presenting device 10 is, for example, a display device which includes a display. Alternatively, the presenting device 10 may be communication terminal equipment, such as a tablet terminal, which a medical expert brings with him/her.

Image data which indicates a captured image of tissue is transmitted from the external device 8 to the image analyzing device 1a. In a case where the image analyzing device 1a receives the image data, an image analyzing section 4 analyzes the image, and determines (i) whether a cell is a cancer cell and (ii) the type of cancer. The determination result transmitting section 9 transmits a result of determination to the presenting device 10 or the external device 8.

The image analyzing system 100a includes the external device 8a, the image analyzing device 1a, and the presenting device 10. The external device 8a and the image analyzing device 1a are each connected to an information communication network 50 such as the Internet. This allows the external device 8a and the image analyzing device 1a to transmit/receive data to/from each other. The presenting device 10 is connected to the external device 8a.

That is, the image analyzing device 1a is capable of (i) receiving, from the external device 8a, an image captured at a distant place, (ii) analyzing the image, and then (iii) transmitting a result of determination to the presenting devices 10. The presenting devices 10 can be each a device which is connected to the external device 8a or can be alternatively a device which is independent of the image analyzing device 1a and the external device 8a.

[Software Implementation Example]

Control blocks (particularly, the image quality determining section 40, the binarizing section 41, the Betti number calculating section 42, and the cancer determining section 43) of the image analyzing device 1, 1a may be realized by a logic circuit (hardware) provided in an integrated circuit (IC chip) or the like or can be alternatively realized by software.

In the latter case, the image analyzing device 1, 1a includes a computer which executes instructions of a program that is software realizing the foregoing functions. The computer, for example, includes at least one processor and at least one computer-readable storage medium storing therein the program. An object of the present invention can be achieved by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be made available to the computer via any transmission medium (such as a communication network and a broadcast wave) which allows the program to be transmitted. Note that an aspect of the present invention can also be achieved in the form of a computer data signal in which the program is embodied via electronic transmission and which is embedded in a carrier wave.

The present invention is not limited to the embodiments, but can be altered by a skilled person in the art within the scope of the claims. The present invention also encompasses, in its technical scope, any embodiment derived by combining technical means disclosed in differing embodiments.

Aspects of the present invention can also be expressed as follows:

An image analyzing method in accordance with a first aspect of the present invention is a method for analyzing a captured image of tissue, including: a binarizing step (step S2) of carrying out a binarizing process a plurality of times with respect to a single captured image so as to generate a plurality of binarized images, the binarizing process being carried out in such a manner that each time a binarization reference value is varied, the binarizing process is carried out; a region number calculating step (step S3) of calculating a region number, which indicates the number of hole-shaped regions, with respect to each of the plurality of binarized images which have been generated in the binarizing step; and a determining step (step S4) of determining a type of cancer occurring in a cell included in the tissue, on the basis of the binarization reference value which has been applied at a time of generation of one of the plurality of binarized images with respect to which one the region number has a given value.

Note, here, that the "tissue" indicates biological tissue including cells of a subject. Note, here, that the "hole-shaped regions" indicate spaces (holes) shown in a captured image which is a two-dimensional plane. As a process of calculating the number of hole-shaped regions, a process of calculating a one-dimensional Betti number with respect to each of the plurality of binarized images can be carried out. Note that a known program for calculating a Betti number from an image may be used.

In a case where a cell becomes cancerous, the amount of chromatin in a cell nucleus in the cell is increased. Chromatin in a cell nucleus is considered to be linear, and is three-dimensionally distributed. The inventors focused their attention on a relationship between the depth of focus and contrast, and found that, by using binarized images obtained by binarizing a captured image of tissue, it is possible to read information pertaining to a state of presence of chromatin which is three-dimensionally distributed in a cell nucleus. For example, in a case where the amount of chromatin in a cell nucleus is increased, a degree of crowding and a degree of interlacing of the chromatin is increased. That is, it is possible to evaluate the degree of crowding and the degree of interlacing of the chromatin in the cell nuclei on the basis of the number of hole-shaped regions in each of binarized images.

According to the above configuration, a plurality of binarized images are first generated with use of a varied binarization reference value from a captured image of tissue, and a region number, which indicates the number of hole-shaped regions, is calculated with respect to each of the plurality of binarized images. Then, the type of cancer occurring in a cell included in the tissue is determined on the basis of the binarization reference value which has been applied at a time of generation of one of the plurality of binarized images with respect to which one the region number has a given value.

This makes it possible to, with reference to a captured image which is a two-dimensional plane, highly accurately detect canceration of a cell included in tissue and determine (i) whether the cell is a cancer cell or not and (ii) the type of cancer.

The image analyzing method in accordance with a second aspect of the present invention can be arranged so as to, in the first aspect, further include an extracting step (step S1) of extracting an image of a cell nucleus included in the single captured image, the binarizing step (step S2) being carried out with respect to the image of the cell nucleus which image has been extracted in the extracting step.

As described above, chromatin is present in a cell nucleus. According to the above configuration, an image of a cell nucleus is extracted from a captured image of tissue, and binarization is carried out. This makes it possible to appropriately determine the type of cancer occurring in the cell included in the tissue, without being affected by a part other than the cell nucleus.

The image analyzing method in accordance with a third aspect of the present invention can be arranged such that, in the first or second aspect, in the determining step (step S4), the type of the cancer is determined on the basis of a size of a cell nucleus in the cell.

It is known that cell nuclei in some types of cancer cells become large in sizes as compared with a cell nucleus in a normal cell. According to the above configuration, the type of cancer is determined in consideration of the size of a cell nucleus in addition to an increase in amount of chromatin. This makes it possible to determine, in more detail, the type of the cancer.

The image analyzing method in accordance with a fourth aspect of the present invention can be arranged such that, in any one of the first through third aspects, in the determining step (step S4), the type of the cancer is determined on the basis of whether the maximum value of the region number, which has been calculated with respect to each of the plurality of binarized images, is equal to or lower than a given value.

The inventors found that some types of cancer cause the maximum values of region numbers, which are calculated from a plurality of binarized images, to be clearly different from the maximum values of region numbers derived from the other types of cancer. According to the above configuration, it is possible to determine the type of cancer in more detail.

The present invention also encompass (i) an image analyzing program for causing a computer to carry out each step included in the image analyzing method in accordance with any one of the first through fourth aspects and (ii) a storage medium in which the image analyzing program is computer-readably stored.

In order to attain the above object, an image analyzing device (1, 1a) in accordance with a seventh aspect of the present invention is an image analyzing device which analyzes a captured image of tissue, including: a binarizing section (41) which carries out a binarizing process a plurality of times with respect to a single captured image so as to generate a plurality of binarized images, the binarizing section carrying out the binarizing process each time the binarizing section varies a binarization reference value; a region number calculating section (Betti number calculating section 42) which calculates a region number, which indicates the number of hole-shaped regions, with respect to each of the plurality of binarized images which have been generated; and a cancer determining section (43) which determines a type of cancer occurring in a cell included in the tissue, on the basis of the binarization reference value which has been applied at a time of generation of one of the plurality of binarized images with respect to which one the region number has a given value. According to the above configuration, an effect similar to that brought about by the image analyzing method in accordance with the first aspect of the present invention is brought about.

In order to attain the above object, an image analyzing system (100, 100a) in accordance with an eighth aspect of the present invention is an image analyzing system including: an image analyzing device (1, 1a) described in the seventh aspect; an external device (8) which transmits, to the image analyzing device, image data which indicates a single captured image of tissue; and a presenting device (10) which obtains a result of determination made by the image analyzing device (1, 1a) and presents the result of the determination.

According to the above configuration, it is possible to (i) receive, with use of the external device (8), an image captured at a distant place, for example, (ii) analyze the image, and (iii) present a result of determination to a user at a distant place. Note, here, the user may be a medical expert, such as a doctor.

REFERENCE SIGNS LIST 1, 1a Image analyzing device
2 Image obtaining section
3 Storage section
4 Image analyzing section
5 Display control section
6 Display device
7 Primary storage section
8 External device
9 Determination result transmitting section
10 Presenting device
40 Image quality determining section
41 Binarizing section
42 Betti number calculating section (region number calculating section)
43 Cancer determining section
100, 100a Image analyzing system
S1 Extracting step
S2 Binarizing step
S3 Region number calculate step
S4 Determining step

The invention claimed is:

1. A method for analyzing a captured image of tissue, comprising:
a binarizing step of carrying out a binarizing process a plurality of times with respect to a single captured image so as to generate a plurality of binarized images, the binarizing process being carried out in such a manner that each time a binarization reference value is varied, the binarizing process is carried out;
a region number calculating step of calculating a region number, which indicates the number of hole-shaped regions, with respect to each of the plurality of binarized images which have been generated in the binarizing step; and
a determining step of determining a type of cancer occurring in a cell included in the tissue, on the basis of the binarization reference value which has been applied at a time of generation of one of the plurality of binarized images with respect to which one the region number has a given value.

2. The method as set forth in claim 1, further comprising:
an extracting step of extracting an image of a cell nucleus included in the single captured image,
the binarizing step being carried out with respect to the image of the cell nucleus which image has been extracted in the extracting step.

3. The method as set forth in claim 1, wherein in the determining step, the type of the cancer is determined on the basis of a size of a cell nucleus in the cell.

4. The method as set forth in claim 1, wherein in the determining step, the type of the cancer is determined on the basis of whether the maximum value of the region number, which has been calculated with respect to each of the plurality of binarized images, is equal to or lower than a given value.

5. A computer-readable non-transitory storage medium in which an image analyzing program is stored, the image analyzing program being for causing a computer to carry out each step included in the method recited in claim 1.

6. An image analyzing device which analyzes a captured image of tissue, comprising:
a binarizing section which carries out a binarizing process a plurality of times with respect to a single captured image so as to generate a plurality of binarized images, the binarizing section carrying out the binarizing process each time the binarizing section varies a binarization reference value;
a region number calculating section which calculates a region number, which indicates the number of hole-shaped regions, with respect to each of the plurality of binarized images which have been generated; and a cancer determining section which determines a type of cancer occurring in a cell included in the tissue, on the basis of the binarization reference value which has been applied at a time of generation of one of the plurality of binarized images with respect to which one the region number has a given value.

7. An image analyzing system comprising:
an image analyzing device recited in claim 6;
an external device which transmits, to the image analyzing device, image data which indicates a single captured image of tissue; and
a presenting device which obtains a result of determination made by the image analyzing device and presents the result of the determination.

* * * * *